United States Patent [19]

Tahvonen

[11] Patent Number: 4,595,589

[45] Date of Patent: Jun. 17, 1986

[54] FUNGISTATIC METHOD

[75] Inventor: Risto Tahvonen, Helsinki, Finland

[73] Assignee: Kemira Oy, Helsinki, Finland

[21] Appl. No.: 475,805

[22] Filed: Mar. 16, 1983

[30] Foreign Application Priority Data

Mar. 30, 1982 [FI] Finland ................................. 821099

[51] Int. Cl.$^4$ ...................... A01N 63/00; C12N 3/00; C12N 1/20; C12N 1/02
[52] U.S. Cl. ...................................... 424/93; 435/242; 435/253; 435/261; 435/886; 47/DIG. 11
[58] Field of Search ............... 435/242, 253, 254, 261, 435/822, 886; 424/93

[56] References Cited

U.S. PATENT DOCUMENTS

| | | | |
|---|---|---|---|
| 3,892,850 | 7/1975 | Struyk et al. | 435/76 |
| 3,956,276 | 5/1976 | Hata et al. | 424/181 |
| 3,956,487 | 5/1976 | Hata et al. | 424/181 |
| 4,007,267 | 2/1977 | Kishi et al. | 435/128 |
| 4,011,391 | 3/1977 | Horii et al. | 435/85 |
| 4,089,947 | 5/1978 | Horii et al. | 435/128 |
| 4,133,876 | 1/1979 | Hamill et al. | 424/121 |
| 4,225,585 | 9/1980 | Kida et al. | 424/181 |
| 4,315,922 | 2/1982 | Hagenmaier et al. | 424/180 |
| 4,534,965 | 8/1985 | Brown et al. | 435/886 |

FOREIGN PATENT DOCUMENTS 1097189 4/1965 United Kingdom .

OTHER PUBLICATIONS

Bergys Manual of Determinative Biology 8th Ed. Buchanan Ed. pp. 804–819.

Tarhan, G., Z Pflanzenkr Pflanzenschutz, 88 (7), pp. 422–434, (1981), "A New Race of *Streptomyces Ochraceiscleroticus* in the Biological Control of Some Soil-Borne Plant Pathogens, 2. in vivo Studies on the Possibilities of Using C-2-9 Isolate Against Some Important Diseases".

Primary Examiner—Thomas G. Wiseman
Assistant Examiner—R. Thomas Gallegos
Attorney, Agent, or Firm—Biebel, French & Nauman

[57] ABSTRACT

The invention relates to a method for preventing fungus diseases in plants grown in, for example, a bed containing peat, by adding to the vegetation or the soil *streptomyces griseaviridis* stains ATCC 39271, 39272 and 39273. The aqueous suspension preferably contains at least $10^5$ spores/ml, and at least 10 ml of the aqueous suspension is spread per one m$^2$, or the seeds are immersed in the aqueous suspension.

14 Claims, 2 Drawing Figures

FUNGISTATIC METHOD

BACKGROUND OF THE INVENTION

The present invention relates to a method for the control of fungus diseases in plants grown in a bed containing peat. The invention further relates to novel *Streptomyces griseoviridis* strains and their use.

Attempts have been made to control plant diseases in greenhouses by means of disinfection and replacement of the soil and by means of various cultural practices and control by chemicals. So far, biological control has hardly been used as regards plant diseases. However, certain important crops such as lettuce, cucumber and tomato suffer from detrimental soil-spread diseases which have not been possible to control owing to restrictions of use of chemical control agents and hazard periods due to possible residues, or owing to a lack of sufficiently effective products. If some biological control method could be developed for and applied to cultivations of this type, it would be a significant step of progress for both the producer and the consumer.

It is previously known to isolate the antibiotic produced by the actinomycete fungi of the Streptomyces family and to use this antibiotic as a fungistat. However, the action of the antibiotic is short-term, and it ceases when the antibiotic has been consumed.

The object of the present invention is therefore to produce an *Streptomyces griseoviridis* strain of the Streptomyces family, a strain which thrives in soil and is capable to compete with other micro-organisms in it.

SUMMARY OF THE INVENTION

It has now been observed surprisingly that by adding *Streptomyces griseoviridis* strains ATCC 39271, ATCC 39272 and ATCC 39273 of the Streptomyces family to the soil or to the vegetation, both soil-spread and seed-spread diseases can be controlled durably and effectively. *Streptomyces griseoviridis* strains of the Streptomyces family thriving in the vegetation or the soil, usable in the method according to the invention, have been found in, for example, peat, and they can be isolated from peat by conventional methods.

DESCRIPTION OF THE PREFERRED EMBODIMENTS

*Streptomyces griseoviridis* strains ATCC 39271, 39272, 39273 of the Streptomyces family, isolated from peat, can be added to the soil or the vegetation in the form of an aqueous suspension, for example, by spraying. In such a case the aqueous suspension preferably contains at least about 100,000 spores per one milliliter. The quantity of spraying is preferably at least 10 ml/m$^2$. Alternatively, the seeds can be immersed in the aqueous suspension before being planted.

The *Streptomyces griseoviridis* strains of the Streptomyces family according to the invention either inhibit the action of diseases on the seed or limit their spreading from an infected seedling to a healthy seedling.

Figure 1:
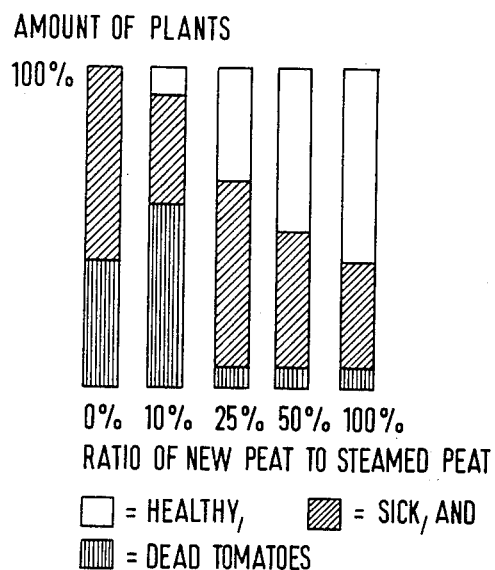
Figure 2:
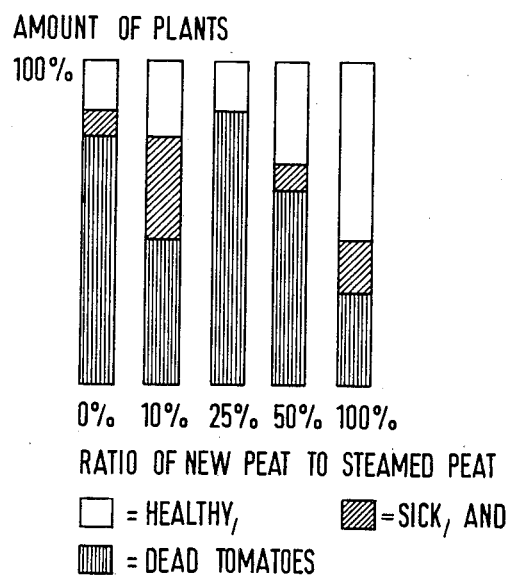

This advantageous fungistatic property is clearly manifest in biological control of plant diseases when peat which contains *Streptomyces griseoviridis* strain of the Streptomyces family according to the invention is added to the soil after disinfection, whereby the soil acquires a useful microbe base. FIGS. 1 and 2 show this effect, the pathogen or the detrimental disease being the Fusarium oxysporum wilt.

The method according to the invention makes use of the fungistatic properties of the *Streptomyces griseoviridis* strains ATCC 39271, 39272 and/or 39273 present in peat. These *Streptomyces griseoviridis* strains have proven to be effective inhibitors of the growth of, for example, the following pathogens: *Alternaria brassicicola, Fusarium culmorum, F. oxysporum, Helminthosporium sativum, Rhizoctonia solani, Phoma exicue* var. *exicue, P. exicue* var. *foveata,* Pythium spp., *Sclerotinia sclerotiorum, Botrytis cinerea.*

The invention is described below in greater detail with the aid of examples.

EXAMPLE 1

Alternaria and Rhizoctomia early blights of cabbage were controlled effectively by means of an actinomycete fungus treatment of the seeds. Table 1 shows the fungistatic properties of *Streptomyces griseoviridis* strains ATCC 39271 and 39272 according to the invention.

TABLE 1

Action of various *Streptomyces griseoviridis* strains, used for seed treatment, on seed-spread early blight of cabbage. *Alternaria brassicicola* seed contamination

| *Streptomyces griseoviridis* strain | Seedlings | Healthy and viable ones at end of experiment |
|---|---|---|
| ATCC 39271 | 91 | 84 |
| ATCC 39272 | 107 | 78 |
| Infected seed only | 16 | 3 |
| Healthy seed | 100 | 100 |

There are individual differences among the various strains of actinomycete fungi. The best result as regards different diseases and plants varied according to the treatment method and the dilution. For example, with cabbage the most effective result was obtained using seed treatment, but with barley using soil treatment.

The growing of *Streptomyces griseoviridis* strains according to the invention in laboratory conditions is rapid, easy and economical. The actinomycete fungi grow and spread rapidly and effectively in, for example, a bed of steamed peat, either when sprayed into the planted layer or when inoculated together with the seeds. About 2-3 weeks after the inoculation a white, lime-like growth can be observed on the surface of the peat and also inside it. This is *Streptomyces griseoviridis,* and the present invention is based on its surprising action on detrimental pathogens of plants.

A few additional examples are presented below to illustrate the surprisingly observed action of the *Streptomyces griseoviridis* strains according to the invention on detrimental plant diseases.

EXAMPLE 2

Excellent results were achieved by using actinomycete fungi to control early blight, *Alternaria brassicicola.* The efficacies of 12 strains were compared in the experiments by using contaminated cauliflower seedlings and both seed and soil treatment. Strain ATCC 39271 had the most uniform action, always among the best. The results are shown in Table 2 below.

TABLE 2

| | Seedlings, %/Healthy seedlings, % | |
|---|---|---|
| | Seed treatment | Soil treatment |
| Healthy Seeds | 89.8/89.8 | 89.8/89.8 |
| Controls (infected) | 14.7/5.6 | 14.7/5.6 |
| *Streptomyces griseoviridis* | 81.4/71.1 | 52.8/35.0 |

TABLE 2-continued

| | Seedlings, %/Healthy seedlings, % | |
|---|---|---|
| | Seed treatment | Soil treatment |
| Strain ATCC 39271 | | 5 |

Seed treatment was more effective than soil treatment.

A comparison between an aqueous suspension of *Streptomyces griseoviridis* and a nutrient solution suspension of *Streptomyces griseoviridis* did not show greater differences as regards concentrated solutions. But when the solutions are diluted even to $10^{-1}$, the effectiveness of the aqueous suspension decreases, whereas the effectiveness of a nutrient-containing solution remains almost unchanged even when diluted to $10^{-6}$. Also, no differences in effectiveness can be observed if the *Streptomyces griseoviridis* has been pre-grown in nutrient agar or taken directly from its growth solution. If strains of different efficacy are mixed with each other, the final result is usually in accordance with that of the weakest strain.

EXAMPLE 3

Lettuce seedlings were sprayed just before planting with a *Streptomyces griseoviridis* suspension (ATCC 39271) (about 1 ml/seedling). Some of them were subjected to two further treatments later.

Sets of two rows were alternately contaminated (by means of an automatic pipette around the base of the plant) with *Botrytis cinerea* or *Rhizoctonia solani*, and alternatively left uncontaminated. The latter disease strain was so weakened that there were hardly any differences in the experiment, but as regards Botrytis, the disease occurrence was clearly reduced and the crops were improved even in the uncontaminated rows. The results are shown in Table 3 below.

TABLE 3

| | Disease occurrence (index 0–3)*/crop (kg/spot) | | |
|---|---|---|---|
| Botrytis cinerea | Control | Seedlings treated | Seedlings treated + 2 additional treatments |
| Infected plants 20 plants/spot | 2.22/2.2 | 1.45/2.8 | 1.43/3.0 |
| Adjacent plants 30 plants/spot | 0.93/4.7 | 0.63/5.1 | 0.48/5.2 |

*0 = healthy
3 = saleable

EXAMPLE 4

Manifest control action on diseases affecting the base of cucumber (mainly *Fusarium oxysporum*) could be observed as regards strain ATCC 39271. The incoulation was by spraying the peat surface at the base of the cucumber plant. The results are shown in Table 4 below.

TABLE 4

| | Untreated | Treated |
|---|---|---|
| Disease occurrence: index 0–3 | 1.37 | 1.07 |
| Healthy plants, % | 32 | 50 |

EXAMPLE 5

The effectiveness of *Streptomyces griseoviridis* strain ATCC 39271 in controlling the *Potrypis cinera* was experimented with by spraying strawberry variety Senga Sengana three times during the crop-growing year with a 1% aqueous solution of the above-mentioned *Streptomyces griseoviridis* strain, as calculated from a nutrient-solution suspension. The crop was harvested 8 times, and the quantity of the crop is expressed in the table below in kg/ha. The results are shown in Table 5 below.

TABLE 5

Control of *Potrypis cinerea* of strawberry, variety Senga Sengana, 1st year of growing crop.
Spot size 1 × 10 m. 4 replications.
Sprayings carried out June 7, +11 °C.; June 14, +8 °C.; and June 22, +13 °C.
Crop harvested 8 times.

| | Crop, healthy | | Crop, moldy | | Crop, total | |
|---|---|---|---|---|---|---|
| Test member | kg/ha | ratio | kg/ha | ratio | kg/ha | ratio |
| 1 untreated | 12 841 | 100 | 296 | 100 | 13 137 | 100 |
| 2 Ronilan 3 × 0.1% | 11 694 | 91 | 169 | 57 | 11 863 | 90 |
| 3 Euparen 3 × 0.25% | 13 639 | 106 | 208 | 70 | 13 847 | 105 |
| 4 *Streptomyces griseoviridis* 3 × 1%[1] | 14 384 | 112 | 280 | 94 | 14 664 | 112 |

[1]For application, dilution was 1% from nutrient solution suspension

"Ronilan" is a commercial product in which the active ingredient is vinclozolin. "Euparen" is a commercial product in which the active ingredient is dichlorofluamid.

It can be seen that the strawberry plants sprayed with an aqueous suspension of *Streptomyces griseoviridis* strain ATCC 39271 yielded not only a more substantial crop but also a greater quantity of healthy strawberries.

EXAMPLE 6

The effect of *Streptomyces griseoviridis* strain ATCC 39271 on grain crops was studied by cultivating seeds of Karri barley which had first been immersed in an aqueous suspension of the said *Streptomyces griseoviridis* thereafter dried. The results are shown in Table 6 below.

TABLE 6

Effect of Streptomyces treatment of the seed of Karri barley (10% dilution for application + 10% dilution from nutrient, wetting of the seeds + drying) on grain crop in different types of crop rotation.

| Plants in preceding years | Untreated crop kg/ha | Streptomyces treated seed (ATCC 39271) crop addition kg/ha (%) |
|---|---|---|
| 1 yr barley + fallow | 4755 | +837 (17.6%) |
| 2 yr barley + fallow | 4500 | +948 (21.0%) |
| 3 yr barley + fallow | 4563 | +102 (2.2%) |
| 6 yr barley | 4527 | +285 (6.3%) |
| horse bean** | 5241 | +165 (3.1%) |
| oats** | 4935 | +15 (<1%) |
| rape** | 4764 | +792 (16.6%) |
| diversified rotation* | 5295 | +474 (9.0%) |
| $\bar{x}$ | 4823 | +452 (9.4%) |

*oats, horse bean, rape
**every second year

The above table shows that the treatment of barley seed by means of a water suspension of an *Streptomyces griseoviridis* strain according to the invention improved the crop in all the cases studied.

EXAMPLE 7

Finally, the disease inhibiting effect of *Streptomyces griseoviridis* strains ACTT 39271, 39272 and 39273 against various fungus diseases was studied on a nutrient bed. The results are shown below in Table 7.

TABLE 7

The disease inhibiting action of Streptomyces isolates ATCC 39271, ATCC 39272 and ATCC 29273 on various fungus diseases in growth experiments on a nutrient bed

| Test fungus | Isolates ATCC No. | | |
|---|---|---|---|
| | 39271 | 39272 | 39273 |
| | Inhibiting action, 0-3* | | |
| *Phomopsis sclerotioides* | 1 | 1 | 2 |
| *Pythium ultimum* | 0 | 1 | 1 |
| *Rhizoctonia solani* | 3 | 1 | 3 |

*0 = ineffective, 1 = average, 2 = strong, 3 = very strong

FORMULATION AND STORAGE

One usable method for preparing an aqueous suspension which contains a *Streptomyces griseoviridis* strain according to the invention is to isolate an actinomycete fungus grown in nutrient solution and to homogenize it in sterilized water. Thereafter the suspension is centrifuged and the moist spore pulp is stored in a plastic bag. For use, the contents of the plastic bag are suspended in water.

In studies of the effect of the storing temperature it was observed that, when *Streptomyces griseoviridis* spores were stored in distilled water or in a physiological saline solution, no storage problems were encountered within half a year at $-20°$ C., $+4°$ C. or $+20°$ C.

One petri dish of *Streptomyces griseoviridis* contains about $10^{10}$ spores, which suspended in, for example, 50 ml of water suffices well for the immersion of a couple of kilograms of cabbage seeds (300 g seeds/ha).

What is claimed is:

1. A method for controlling fungus diseases in plants which comprises:
    applying at least one *Streptomyces griseoviridis* strain selected from the group consisting of ATCC 39271, ATCC 39272, and ATCC 39273 to soil, seed, or vegetation in an amount effective for controlling plant fungus diseases, said strain being indigenous to peat and being effective in controlling plant fungus diseases.

2. The method of claim 1 wherein said aqueous suspension contains at least about 100,000 spores/ml.

3. The method of claim 2 wherein said aqueous suspension is applied to the soil at a rate of at least 1 dl/m$^2$.

4. The method of claim 2 wherein said aqueous suspension is applied to the vegetation in an amount of at least 1 dl/m$^2$.

5. The method of claim 2 wherein said strain is applied by immersing seeds in said aqueous suspension.

6. The method of claim 1 wherein said strain is applied by steaming peat, inoculating said peat with said strain, and adding said inoculated peat to the soil.

7. The method of claim 1 wherein said strain is ATCC 39271.

8. The method of claim 1 wherein said strain is ATCC 39272.

9. The method of claim 1 wherein said strain is ATCC 39273.

10. A biologically pure culture of a *Streptomyces griseoviridis* strain selected from the group consisting of ATCC 38271, ATCC 39272, and ATCC 39273, said strain being indigenous to peat and being effective in controlling fungus diseases in plants.

11. The biologically pure culture of claim 10 wherein said strain is ATCC 39271.

12. The biologically pure culture of claim 10 wherein said strain is ATCC 39272.

13. The biologically pure culture of claim 10 wherein said strain is ATCC 39273.

14. The method of claim 9, wherein said strain is applied to the soil in the form of an aqueous suspension.

* * * * *